United States Patent [19]

Miyashita et al.

[11] Patent Number: 5,391,282
[45] Date of Patent: Feb. 21, 1995

[54] SYSTEM FOR DETERMINING DETERIORATION OF OXYGEN CONCENTRATION SENSOR

[75] Inventors: Yukio Miyashita; Hiroshi Ohno; Shinichi Kubota, all of Wako, Japan

[73] Assignee: Honda Giken Kogyo Kabushiki Kaisha, Tokyo, Japan

[21] Appl. No.: 152,090

[22] Filed: Nov. 15, 1993

Related U.S. Application Data

[63] Continuation of Ser. No. 878,596, May 5, 1992, abandoned.

[30] Foreign Application Priority Data

Jun. 14, 1991 [JP] Japan .................................. 3-169456

[51] Int. Cl.⁶ ............................................. G01N 27/26
[52] U.S. Cl. .................................. 204/401; 204/406; 204/421; 204/425; 204/426
[58] Field of Search ............... 204/401, 406, 421, 424, 204/425, 426, 427, 428, 429

[56] References Cited

U.S. PATENT DOCUMENTS

| | | | |
|---|---|---|---|
| 4,615,787 | 10/1986 | Yamada et al. | 204/424 |
| 4,767,520 | 8/1988 | Asakura et al. | 204/425 |
| 4,819,602 | 4/1989 | Mieno et al. | 204/401 |
| 4,905,652 | 3/1990 | Nakajima et al. | 204/401 |

*Primary Examiner*—John Niebling
*Assistant Examiner*—Bruce F. Bell
*Attorney, Agent, or Firm*—Nikaido, Marmelstein, Murray & Oram

[57] ABSTRACT

A system for determining an oxygen concentration sensor deterioration caused when foreign particles has clogged at a slit for introducing exhaust gas of an internal combustion engine to block the same. Since it is found by the inventors that sensor output fluctuates greatly between its maximum and minimum values in a TDC interval as the clogging increases, the deviation between the maximum and minimum is first calculated. The calculated deviation is then compared with a reference value and if it exceeds the reference value, the sensor is presumed to deteriorate. The reference value is varied on engine speed, engine load, or an air/fuel ratio of the engine.

18 Claims, 10 Drawing Sheets

SYSTEM FOR DETERMINING DETERIORATION OF OXYGEN CONCENTRATION SENSOR

This application is a continuation of application Ser. No. 07/878,596, filed May 5, 1992, now abandoned.

BACKGROUND OF THE INVENTION

1. Field of the Invention

This invention relates to a system for determining the deterioration of an oxygen concentration sensor and more particularly to a system for determining the deterioration of an oxygen concentration sensor caused by clogging of exhaust gas inlet in the sensor.

2. Description of the Prior Art

A number of techniques have been proposed for accurately measuring the oxygen concentration of exhaust gas from an internal combustion engine. As specific examples there can be mentioned in Japanese Laid-Open Patent Publication Nos. 61-272438 (U.S. Pat. No. 4,842,711), 61-272439 (U.S. Pat. No. 4,767,520, 61-294358, 62-3143, 62-96754 and 1-206251 and Japanese Laid-Open Utility Model Publication No. 64-32442.

Sensors of this type generally have two bodies each composed of oxygen ion-conductive solid electrolyte material disposed opposite each other and each provided with a pair of electric terminals so as to constitute an oxygen-pumping element and a cell element for detecting oxygen concentration. More specifically., the space between the oxygen-pumping element and the cell element is sealed off to form a gas diffusion chamber (diffusion restriction region). The wall of the chamber is provided with a slit or a hole for the introduction of exhaust gas, while ambient air is introduced on the opposite side of the cell element. The electromotive force developed between the terminals of the cell element is detected and compared with a reference voltage. A voltage proportional to the difference between the two voltages is applied across the oxygen-pumping element terminals so as to cause pumping current to flow from the external terminal toward the gas diffusion chamber terminal or vice versa and thus pump in or pump out oxygen ions. The pumping current is thus feedback controlled in the direction for reducing the difference between the electromotive force of the cell and the reference voltage. The pumping current value is converted to a voltage value proportional to the oxygen concentration. As a result it becomes possible to detect the air/fuel ratio over a wide range extending from a rich to a lean mixture.

However, in actual use of this type of oxygen concentration sensor for determining the air/fuel ratio of an internal combustion engine, the exhaust gas inlet slit tends over time to become clogged or plugged by the adhesion of slight or fine metal oxide particles contained in the exhaust gas. When this happens, the detection value deviates further from the actual value as the degree of clogging increases and this decrease in the detection accuracy makes it impossible to control the air/fuel ratio of the engine properly.

The object of this invention is therefore to eliminate the aforesaid problem by providing a system for determining the deterioration of an oxygen concentration sensor which prevents detection error by enabling any clogging of its exhaust gas inlet slit occurring in the course of use to be easily detected and, as a result, when applied for example in a system for controlling the air/fuel ratio of an internal combustion engine enables the air/fuel ratio to be converged on the target value with high precision.

SUMMARY OF THE INVENTION

This invention achieves this object by providing a system for determining the deterioration of an oxygen concentration sensor for an internal combustion engine, the oxygen concentration sensor having an oxygen-pumping element and a cell element, each being composed of a member of a solid electrolytic material having oxygen ion-conductivity and a pair of electrodes having the member interposed therebetween, the oxygen-pumping element and the cell element defining a diffusion restriction region therebetween, voltage applying device connected to said oxygen-pumping element for applying an output voltage, corresponding to a difference between a voltage developed between the electrodes of the cell element and a predetermined reference voltage, to the oxygen-pumping element, and current detecting means connected to the oxygen-pumping element for detecting a value of current flowing therein. The system comprises a first device for detecting a value indicating fluctuation of the detected current, a second device for comparing the detected value with a reference value and a third device for determining the sensor deterioration if the detected value exceeds the reference value.

This will be explained with reference to the graph of FIG. 14, which shows the actually measured fluctuation in the air/fuel ratio detection value (VAF) calculated from the pumping current during one TDC period (top dead center). As will be noted, the pulsation of the exhaust gas causes the detection value to swing between a maximum value VAFmax and a minimum value VAFmin. Moreover, from a comparison of the graph of FIG. 14 based on data measured when the inlet slit clog rate was 15% with the graph of FIG. 15 based on data measured when the inlet slit clog rate was 30%, it is clear that the range of the fluctuation increases with increasing clog rate. Specifically, the deviation VAFDEV between the maximum and minimum values is noticeably larger in the case of FIG. 15. (The "clog rate" referred to here is the ratio of the actual open area of the inlet slit to the prescribed open area thereof expressed as a percentage.)

The aforesaid relationship means that the clog rate can be inferred from the deviation in the detection value. Tests were therefore conducted to determine how the detection value fluctuation range varies as a function of slit clog rate over the range of tolerable rates. The sensor deterioration could then be easily and accurately determined by using the actually measured fluctuation range as a deterioration index.

BRIEF EXPLANATION OF THE DRAWINGS

These and other objects and advantages of the invention will be more apparent from the following description and drawings, in which.

DESCRIPTION OF THE PREFERRED EMBODIMENTS

An embodiment of the invention will now be explained with reference to the drawings, wherein the system according to the invention is incorporated in an air/fuel ratio control system for an internal combustion engine.

Figure 1:
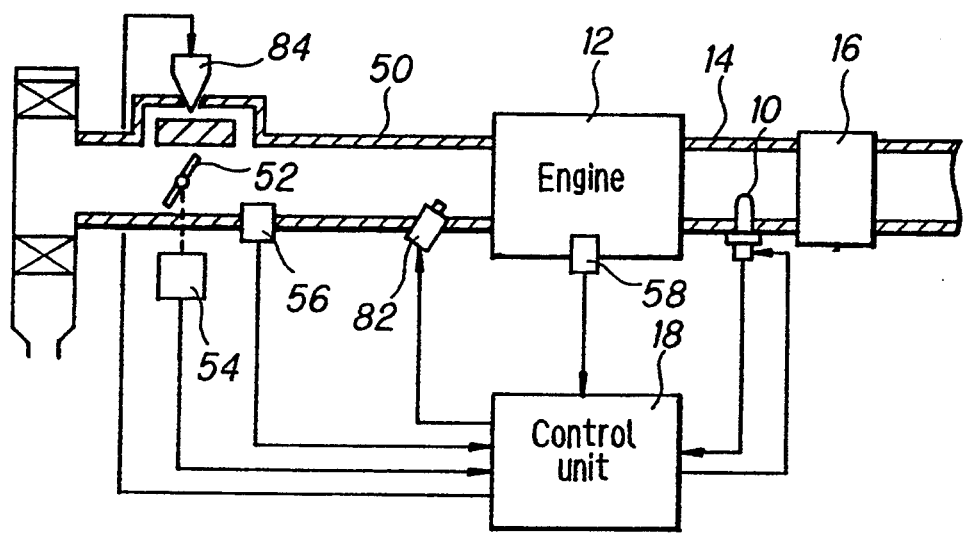
FIG. 1 is an explanatory view showing a system for determining the deterioration of an oxygen concentration sensor according to the invention incorporated in an air/fuel ratio control system for an internal combustion engine.

Referring to FIG. 1, an oxygen concentration sensor (hereinafter called "the oxygen sensor") 10 is installed in an exhaust pipe 14 of an internal combustion engine 12 at a position upstream of a three-way catalytic converter 16. The oxygen sensor 10 is electrically connected with a control unit 18.

Figure 2:
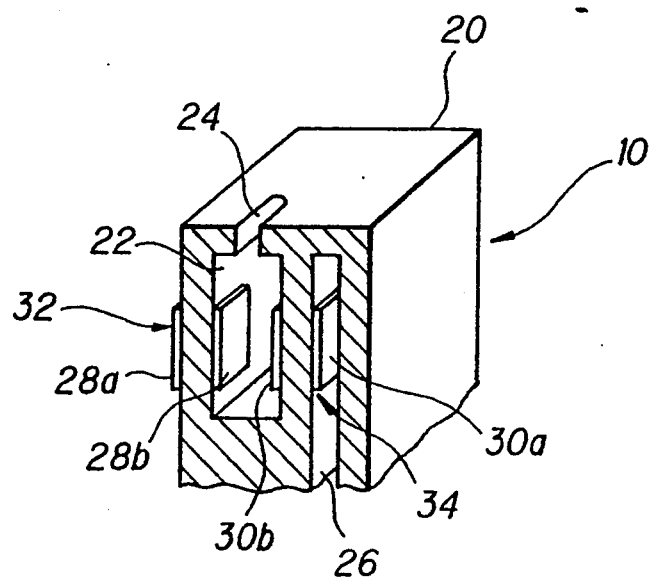
FIG. 2 is an enlarged perspective partial view of an oxygen concentration sensor shown in FIG. 1.

FIG. 2 is an enlarged perspective view of the essential part of the oxygen sensor 10 shown with its protective cover removed. As shown, the oxygen sensor 10 has a main body formed as an oxygen ion-conductive solid electrolytic member 20. The left side of the main body 20 as seen in the drawing is partitioned to form a gas diffusion chamber 22 having an inlet slit 24 which serves for introducing exhaust gas into the gas diffusion chamber 22 from the exhaust pipe 14. On the right side of the main body 20 partitioned from the gas diffusion chamber 22 by a wall is an air reference chamber 26 for introduction of ambient air. A pair of electrodes 30a, 30b are provided on opposite sides of the wall between the gas diffusion chamber 22 and the air reference chamber 26 and a pair of electrodes 28a, 28b are provided on opposite sides of the other side wall of the gas diffusion chamber 22. This arrangement enables the solid electrolytic member 20 and the electrodes 28a, 28b to function as an oxygen-pumping element 32 and the solid electrolytic member 20 and the electrodes 30a, 30b to function as a cell element 34.

Figure 3:
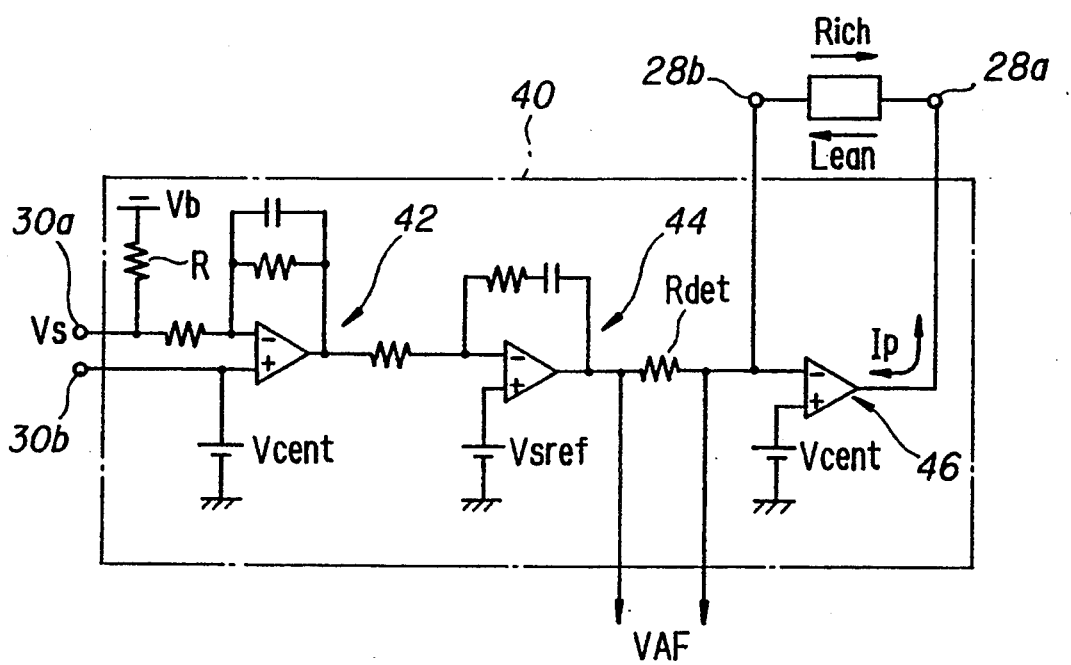
FIG. 3 is a diagram of a detection circuit of the sensor shown in FIG. 2.
Figure 4:
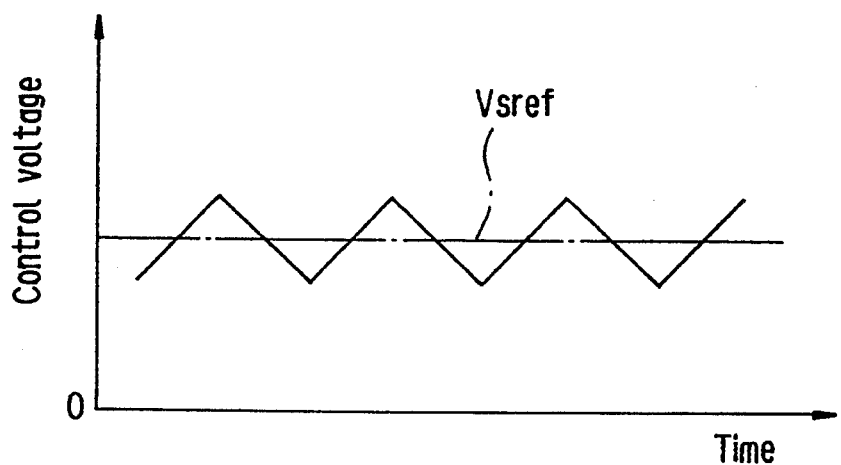
FIG. 4 is an explanatory view illustrating characteristics of an output of a proportional-plus-integral operational amplifier shown in FIG. 3.

FIG. 3 is a schematic diagram of a detection circuit 40 connected with the aforesaid group of electrodes. As will be noted in this diagram, the detection circuit 40 consists of an inverting operational amplifier 42 for detecting and amplifying the electromotive force Vs developed between the cell electrodes 30a, 30b, a proportional-plus-integral operational amplifier 44 for comparing the output of the inverting operational amplifier 42 with a reference voltage Vsref and outputting a control voltage like that shown in FIG. 4, and a voltage/current converter 46 for converting the output of the proportional-plus-integral amplifier 44 to a current value. The detection value VAF is obtained as the voltage across a resistor Rdet. (A prescribed voltage Vcent is applied between the electrodes 28b, 30b on the gas diffusion chamber 22 side.)

The essence of the measuring operation is as follows. When the oxygen concentration in the gas diffusion chamber 22 is lower than a prescribed level, the pumping current Ip flows in the direction of the "lean" arrow, whereby oxygen ions are transferred in the reverse direction and thus pumped out of the gas diffusion chamber. On the other hand, when the oxygen concentration in the gas diffusion chamber 22 is higher than the prescribed level, the pumping current Ip flows in the opposite (rich) direction, whereby oxygen ions are pumped into the gas diffusion chamber. The oxygen concentration in the gas diffusion chamber 22 is thus closed-loop controlled to a prescribed level by the pumping current. The reference voltage Vsref is set at an appropriate value and variations in the pumping current are detected as voltage variations through the detection resistor Rdet. The detected value is then linearized in an appropriate manner to obtain a value in proportion to the oxygen concentration in the exhaust gas over a wide range extending from a lean to a rich mixture.

Returning to FIG. 1, the system is further provided with a throttle position sensor 54 for detecting the degree of opening of a throttle valve 52 in an air intake pipe 50, an absolute pressure sensor 56 for detecting the absolute engine intake air pressure (manifold pressure), and a crankshaft sensor 58 for detecting the crank angle positions of the engine's pistons (not shown). The detection signals from these sensors are forwarded to the control unit 18.

Figure 5:
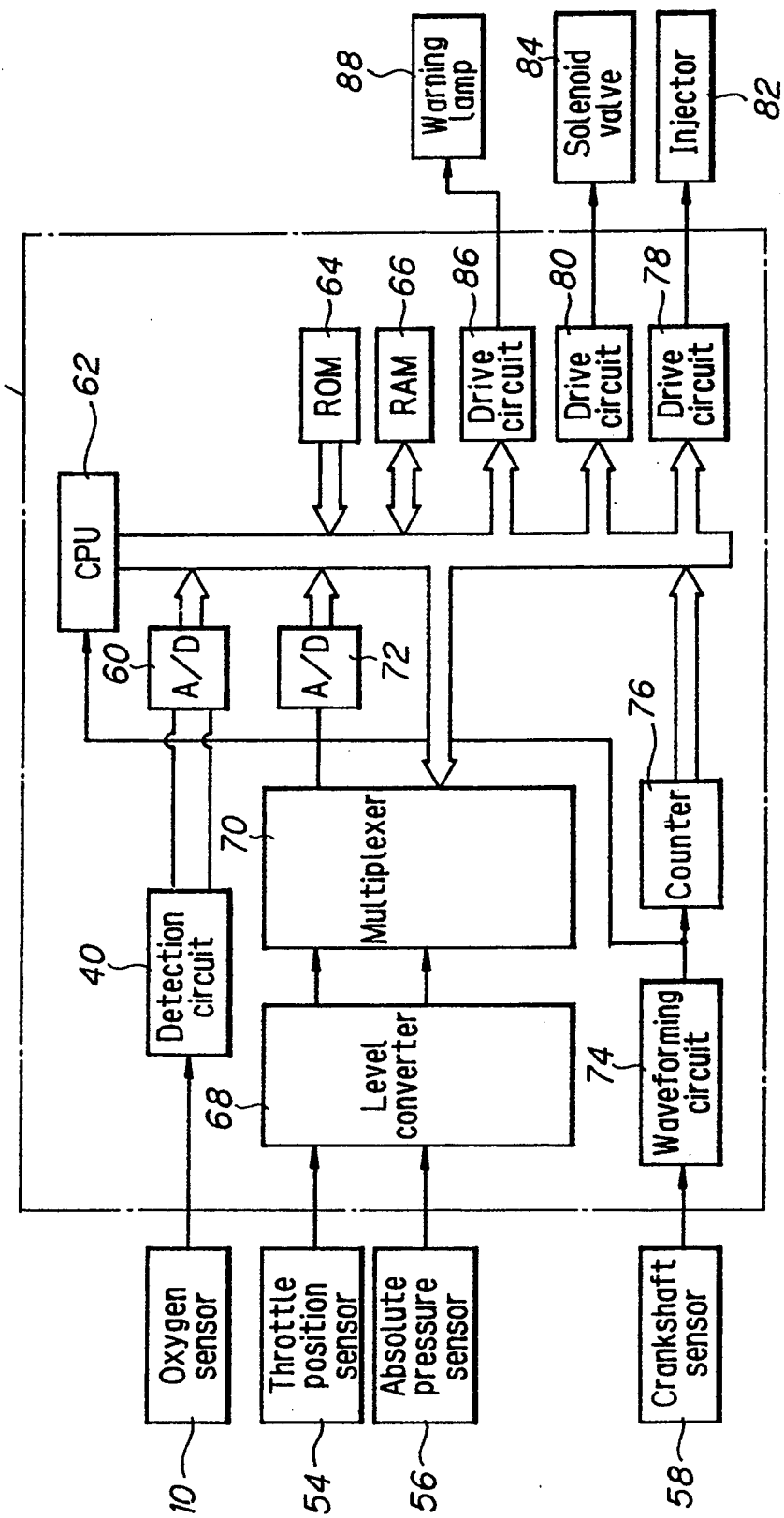
FIG. 5 is a block diagram of a control unit shown in FIG. 1.

The arrangement of the control unit 18 is shown in the block diagram of FIG. 5. The output of the detection circuit 40 is forwarded through an A/D converter 60 to a microcomputer comprising a CPU (central processing unit) 62, a ROM (read-only memory) 64 and a RAM (random access memory) 66 where it is stored in the RAM 66. In addition, the microcomputer receives the analog outputs from the throttle position sensor 54 and the like through a level converter 68, a multiplexer 70 and a second A/D converter 72, and receives the output of the crankshaft sensor 58 through a waveforming circuit 74 and a counter 76. The CPU 62 of the microcomputer calculates the air/fuel ratio control value from the detection values in accordance with commands stored in the ROM 64 and drives an injector 82 and a solenoid valve 84 for secondary air supplier via drive circuits 78, 80. Moreover, when intolerable deterioration (degradation) of the oxygen sensor 10 is detected in the manner to be described later, the CPU 62 turns on an LED or other type warning lamp 88 (not shown in FIG. 1) via a third drive circuit 86.

Figure 6:
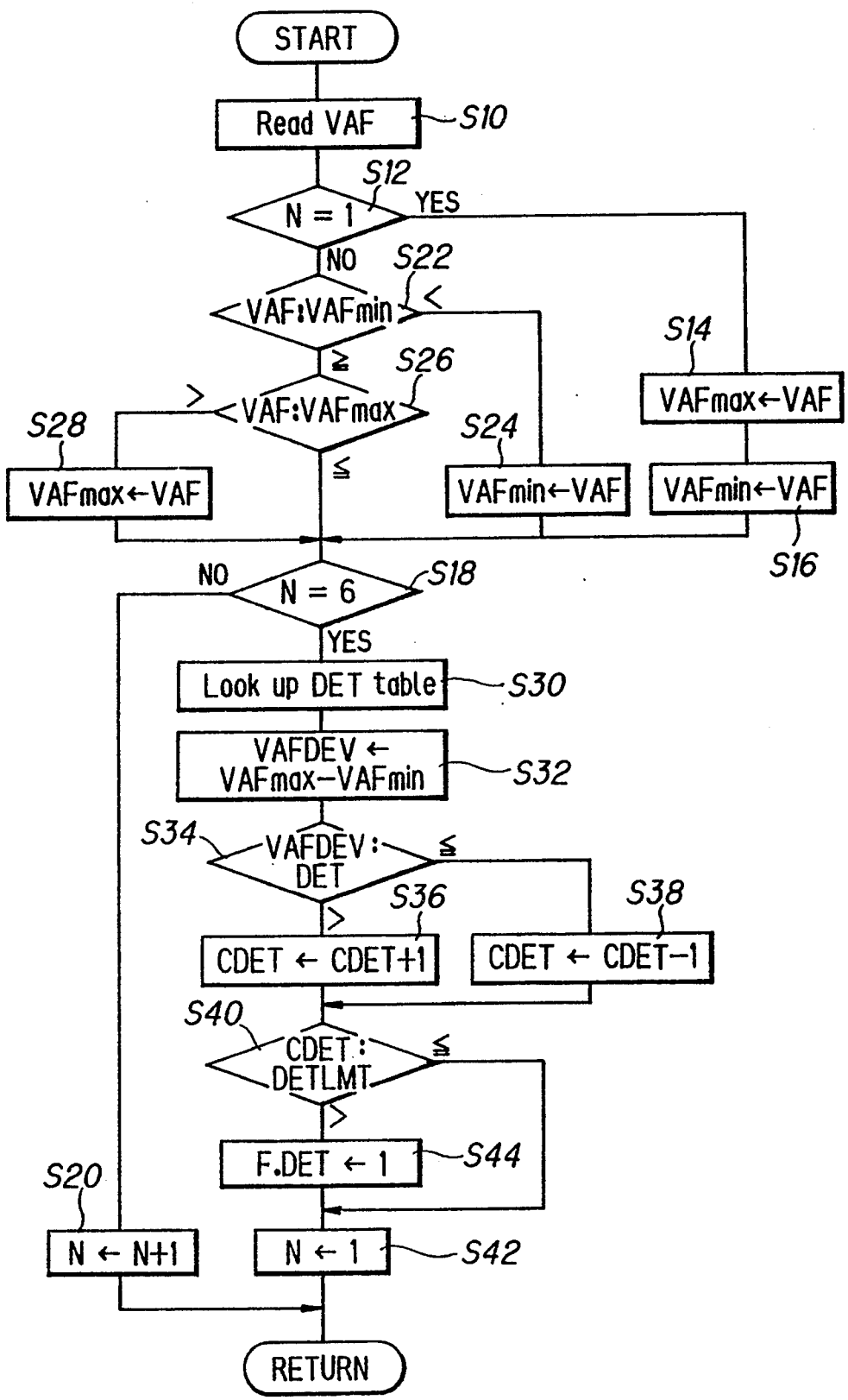
FIG. 6 is a flowchart showing the mode of operation of the unit for determining the sensor deterioration.

The operation of the system will now be explained with reference to the flowchart of FIG. 6. The program according to this flowchart is started in the microcomputer once every 2 ms.

Figure 14:
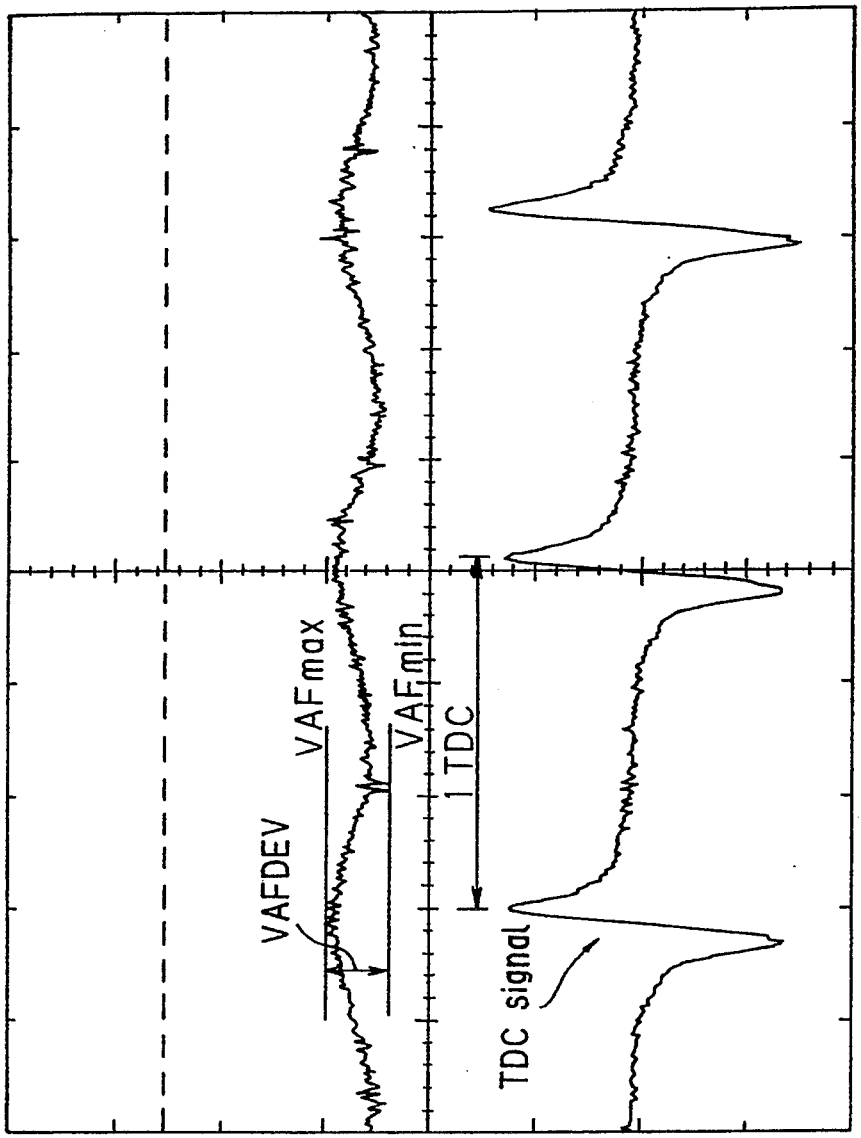
FIG. 14 is a test data illustrating fluctuation of detected values in a TDC (top dead center) period obtained at a clog rate of 15% of an exhaust gas inlet slit.
Figure 15:
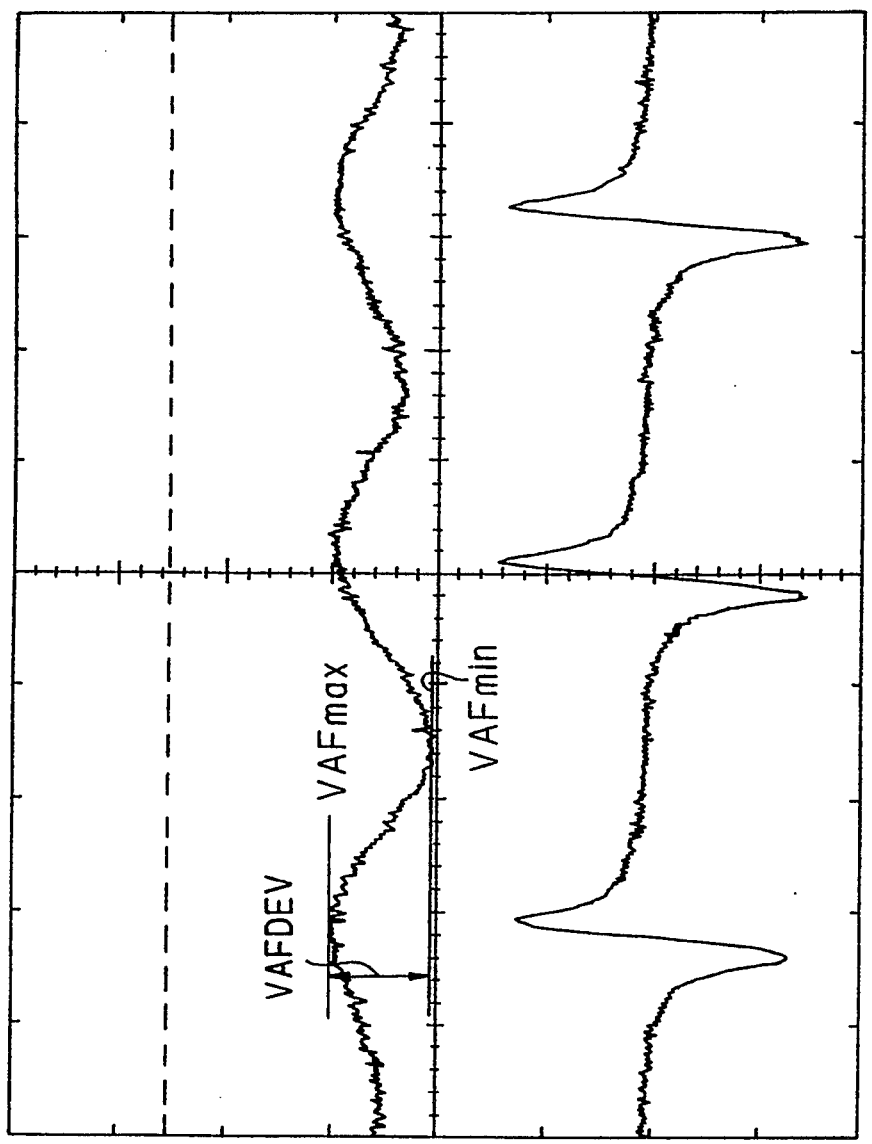
FIG. 15 is a view similar to FIG. 14, but shows a data obtain at the clog rate of 30%.

The pumping current is read in the form of a voltage-converted value VAF in step S10, whereafter it is determined whether or not the value of a counter N is 1 in step S12. As will be remembered from the earlier explanation with respect to FIGS. 14 and 15, the range of fluctuation of the detection value VAF during 1TDC increases as the degree of clogging of the oxygen sensor 10 increases. Since this invention uses this range of fluctuation for discriminating sensor deterioration, several cycles of this program have to be executed at the beginning for collecting data on the maximum value VAFmax and the minimum value VAFmin of the detection value. The counter N is for counting the number of these cycles. While the present embodiment specifies 6 cycles for this purpose, it is alternatively possible to use any other number not smaller than the minimum found necessary for collecting the required data. The data at a clog rate of 15% shown in FIG. 14 was measured at an engine speed of 1870 rpm and a negative manifold pressure of 70 mmHg. The air/fuel ratio under these conditions was 22.7 (not compensated for clogging). While the data at a clog rate of 30% shown in FIG. 15 was measured at the same engine speed and pressure, the air/fuel ratio exceeded 25.0 (not compensated for clogging).

Returning to FIG. 6, the first time the program is started, the result in step S12 is naturally affirmative and the program moves through steps S14 and S16, in which the detected values are temporarily replaced with maximum and minimum values, and through step S18 to step S20 in which the counter value is incremented, whereafter the program is once terminated. In the second and later cycles, VAFmax and VAFmin are successively replaced with the largest and smallest of the values detected in steps S22–S28.

Figure 7:
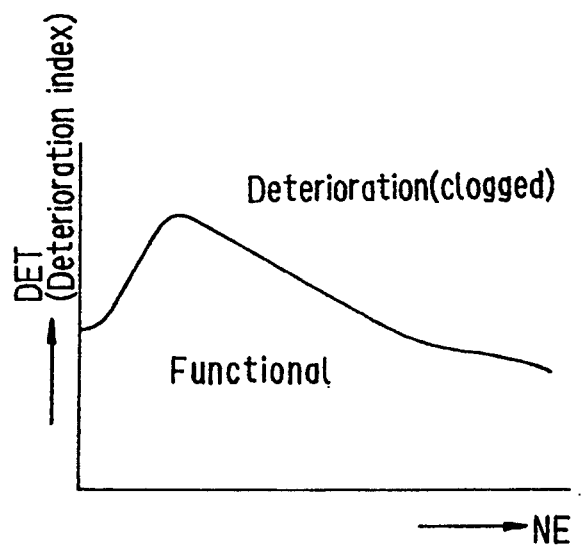
FIG. 7 is an explanatory view illustrating characteristics of a deterioration index used in FIG. 6 flowchart.

When the number of cycles reaches six, the result in step S18 becomes affirmative so that the program goes to step S30 in which a table showing a deterioration index, abbreviated as "DET" here and thereafter, is looked up. As shown by the characteristic curve of FIG. 7, the deterioration index DET is defined in relation to the engine speed NE. The index DET is thus retrieved in this step using the engine speed as address data. As was mentioned earlier, the detection value is affected both by the exhaust gas pulsation and by the degree of clogging of the inlet slit 24 of the oxygen sensor 10. This is thought to be because the higher diffusion resistance resulting from increased clogging of the inlet slit 24 delays the pumping of oxygen ions in and out of the gas diffusion chamber 22 and thus produces fluctuations in the pumping current. Since the pumping current value corresponds to the detection value, any increase in the fluctuation thereof tends to exacerbate the effect of the exhaust gas pulsation. (The reason for defining the deterioration index as a function of the engine speed as shown in FIG. 7 is that the exhaust gas pulsation depends on, and peaks at a prescribed value of, the engine speed. Since this deterioration index is used for judging the degree of clogging of the inlet slit, the range of its variation is established through repeated tests so as to cover the range of tolerable clogging.)

The program then advances to step S32 in which the deviation VAFDEV between maximum and minimum values is calculated and to step 34 in which the calculated value is compared with the deterioration index DET. If the deviation VAFDEV is larger than the deterioration index DET, the value of a counter CDET is incremented in step S36, and if it is not, the value of the counter CDET is decremented in step S38. The result of this method of not simply counting the number of times that the deviation VAFDEV becomes larger than the deterioration index but also taking into account the times that it does not is in effect to make it possible to ascertain how repeatedly (frequently) the deviation exceeds the deterioration index.

In the following step S40, the counter value is compared with an appropriately set deterioration frequency index DETLMT. If the counter value is equal to or smaller than this index, the program advances to step S42 in which the program cycle counter value is reset to 1. As a result, the procedures for collecting data and determining deterioration will be repeated in the next cycle. On the other hand, if the counter value is larger than the index DETLMT, the program moves to step S44 in which the bit of a flag F.DET indicating that the deterioration has progressed to an intolerable degree is set to 1. In this case, since, as was explained earlier, the CPU 62 turns on the warning lamp 88, the operator is made aware of the problem and can have it remedied.

The foregoing arrangement of this embodiment makes it possible to detect the deterioration caused by clogging of the sensor exhaust gas inlet slit simply and accurately merely by determining the range of fluctuation of the detection value of the oxygen sensor and comparing the determined range with an index. Moreover, since the index is set as a function of the engine speed, the effect of the variation of exhaust gas pulsation with engine speed is canceled out, enabling accurate detection of sensor deterioration over a wide range of engine speeds extending from low to high.

Figure 8:
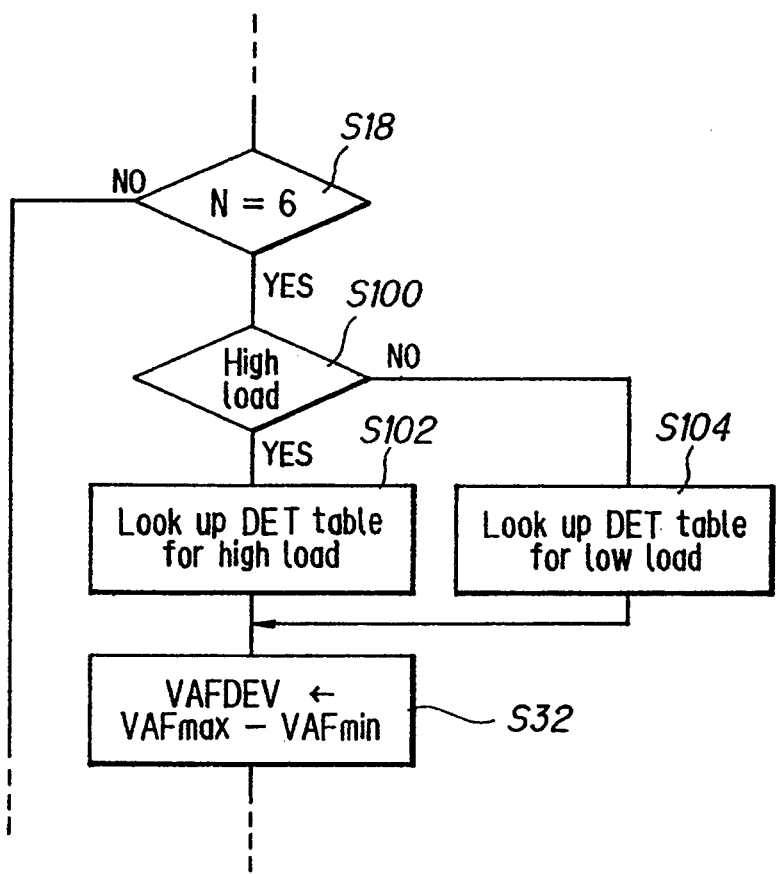
FIG. 8 is a part of a flowchart showing the second embodiment of the invention.
Figure 9:
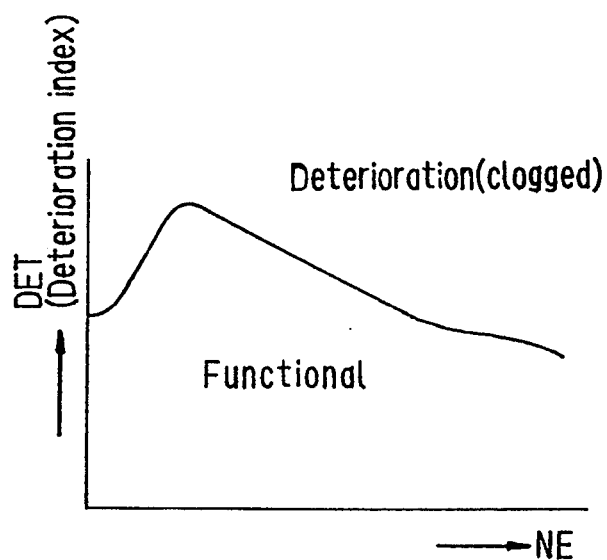
FIG. 9 is an explanatory view illustrating characteristics of a deterioration index for high engine load used in FIG. 8 flowchart.
Figure 10:
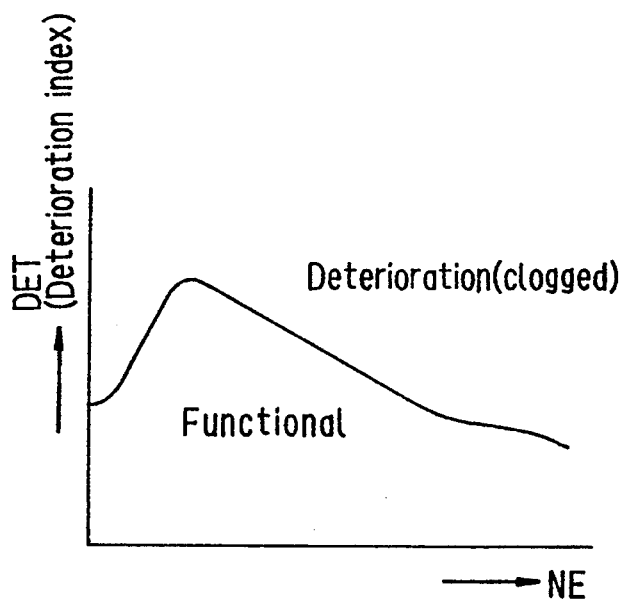
FIG. 10 is a view similar to FIG. 9, but shows a deterioration index for low engine load.

FIG. 8 shows a second embodiment of the invention, which will be explained only in respect of the points in which it differs from the first embodiment. In this embodiment, step S18 is followed by a step (S100) for determining the load state of the engine from the outputs of the absolute pressure sensor 56 etc. referred to earlier and by steps (S102, S104) for, in response to the determination in step S100, setting separate deterioration indices for the high and low load regions. FIG. 9 shows the index characteristics for the high load region and FIG. 10 those for the low load region. The remaining parts of the flowchart of FIG. 8 are the same as those of the flowchart of FIG. 6. Since the effect of the exhaust gas pulsation on the detection value increases with increasing engine load, this embodiment counters this tendency by setting the values for the high load shown in FIG. 9 to be larger than those for the low load shown in FIG. 10. This enables more reliable detection of sensor deterioration under load conditions extending from the low region to the high region.

Figure 11:
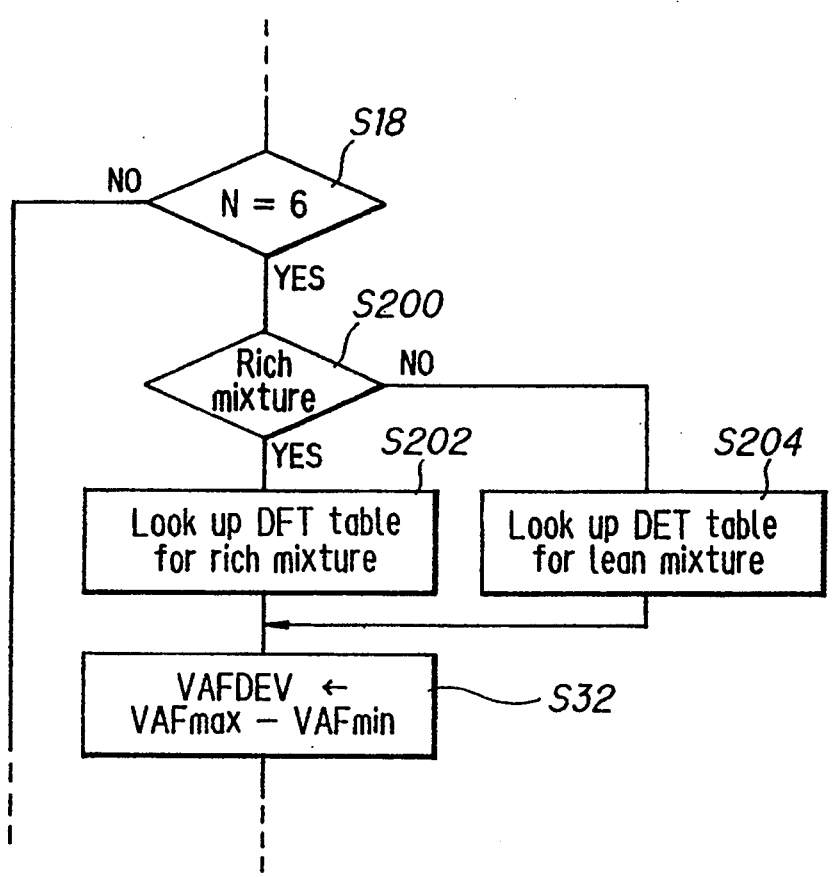
FIG. 11 is a part of a flowchart showing the third embodiment of the invention.
Figure 12:
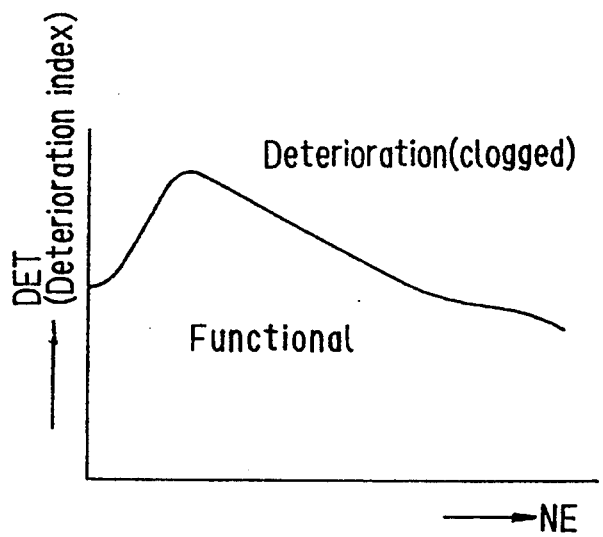
FIG. 12 is an explanatory view illustrating characteristics of a deterioration index for a rich mixture used in FIG. 11 flowchart.
Figure 13:
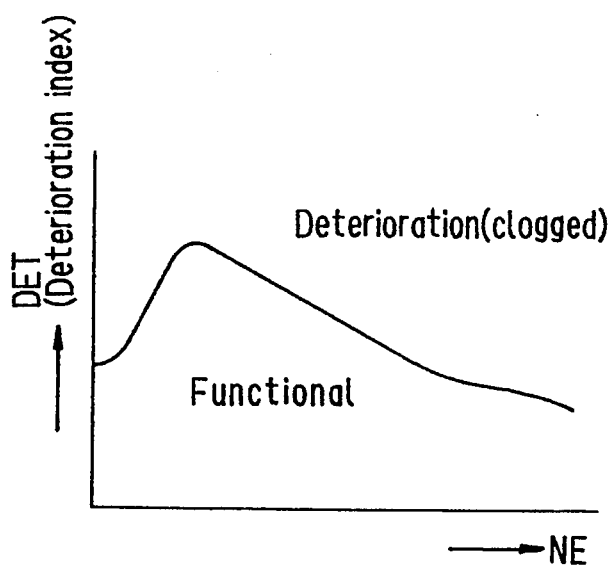
FIG. 13 is a view similar to FIG. 12, but shows a deterioration index for a lean mixture.

FIG. 11 shows a third embodiment of the invention, which will also be explained only in respect of the points in which it differs from the first embodiment. In step S200 a determination is made as to whether the air/fuel ratio is in a rich mixture or a lean mixture and separate deterioration indices are set depending on the result of the determination in steps S202 and S204. FIG. 12 shows the index characteristics for the rich mixture and FIG. 13 those for the lean mixture. Since the effect of the exhaust gas pulsation on the detection value is greater in the rich mixture than in the lean mixture, in this embodiment the index values for the rich mixture are made larger. This makes it possible to accurately take into account the differing detection characteristics between the rich and the lean mixture and thus to detect sensor deterioration with higher reliability. While this embodiment has been explained with respect the case where the index characteristics are selected on the basis of the detected air/fuel ratio it is also possible to obtain substantially the same results by selecting them on the basis of the target air/fuel ratio.

In the embodiments explained in the foregoing, the CPU 62 is programmed to issue a warning upon detection of intolerable sensor degradation. In addition to this, it is possible to establish in advance a plurality of different tolerable clogging limits (deterioration indices) in accordance with the degree to which clogging has advanced and to correct the detection value by changing a correction smoothing coefficient in accordance with the deviation VAFDEV.

As the oxygen sensor in the embodiments described above it is possible to use one having an internal reference oxygen source, as described, for example, in Japanese Laid-Open Patent Publication No. 62-276453.

The present invention has thus been shown and described with reference to the specific embodiments. However, it should be noted that the present invention is in no way limited to the details of the described arrangements but changes and modifications may be made without departing from the scope of the appended claims.

What is claimed is:

1. A system for determining deterioration of an oxygen concentration sensor for an internal combustion engine, said oxygen concentration sensor having an oxygen-pumping element and a cell element, each is composed of a member of a solid electrolytic material having oxygen ion-conductivity and a pair of electrodes having said member interposed therebetween, said oxygen-pumping element and said cell element defining a diffusion restriction region therebetween, voltage applying means connected to said oxygen-pumping element for applying an output voltage, corresponding to a difference between a voltage developed between said electrodes of said cell element and a predetermined reference voltage, to said oxygen-pumping element, and current detecting means connected to said oxygen-pumping element for detecting current flowing as oxygen concentration, said system for determining deterioration of said oxygen concentrator sensor comprising:

current fluctuation detecting means for detecting fluctuation of the detected current from said current detecting means;

fluctuation comparing means for comparing the fluctuation with a reference value; and deterioration determining means for determining the oxygen concentration sensor deterioration if the fluctuation exceeds the reference value.

2. A system according to claim 1, wherein the reference value varies based on engine speed.

3. A system according to claim 2, wherein said detecting means detects the fluctuation by calculating a deviation in a prescribed period between a maximum value and a minimum value of the detected current indicative of oxygen concentration.

4. A system according to claim 3, wherein the set period is a value based on a top dead center interval of said engine.

5. A system according to claim 3, further including counting means for incrementing a number if the fluctuation exceeds the reference value and decrementing the number if the fluctuation does not exceed the reference value, and said determining means determines the oxygen concentration sensor deterioration if the number exceeds a prescribed value.

6. A system according to claim 1, wherein the reference value varies based on engine load.

7. A system according to claim 6, wherein said detecting means detects the fluctuation by calculating a deviation in a set period between a maximum value and a minimum value of the detected current indicative of oxygen concentration.

8. A system according to claim 7, wherein the set period is a value based on a top dead center interval of said engine.

9. A system according to claim 7, further including counting means for incrementing a number if the fluctuation exceeds the reference value and decrementing the number if the fluctuation does not exceed the reference value, and said determining means determines the oxygen concentration sensor deterioration if the number exceeds a prescribed value.

10. A system according to claim 1, wherein the reference value varies based on an air/fuel ratio of the engine.

11. A system according to claim 10, wherein the air/fuel ratio is an actual air-fuel ratio of the engine.

12. A system according to claim 11, wherein said detecting means detects the fluctuation by calculating a deviation in a set period between a maximum value and a minimum value of the detected current indicative of oxygen concentration.

13. A system according to claim 12, wherein the set period is a value based on a top dead center interval of said engine.

14. A system according to claim 12, further including counting means for incrementing a number if the fluctuation exceeds the reference value and decrementing the number if the fluctuation does not exceed the reference value, and said determining means determines the oxygen concentration sensor deterioration if the number exceeds a prescribed value.

15. A system according to claim 10, wherein the air/fuel ratio is a target air-fuel ratio of the engine.

16. A system according to claim 15, wherein said detecting means detects the fluctuation by calculating a deviation in a set period between a maximum value and a minimum value of the detected current indicative of oxygen concentration.

17. A system according to claim 16, wherein the set period is a value based on a top dead center interval of said engine.

18. A system according to claim 16, further including counting means for incrementing a number if the fluctuation exceeds the reference value and decrementing the number if the fluctuation does not exceed the reference value, and said determining means determines the oxygen concentration sensor deterioration if the number exceeds a prescribed value.

* * * * *